United States Patent
Jafari (10) Patent No.: US 7,460,959 B2
(45) Date of Patent: Dec. 2, 2008

(54) SYSTEM AND METHOD FOR ESTIMATING OXYGEN CONCENTRATION IN A MIXED GAS EXPERIENCING PRESSURE FLUCTUATIONS

(75) Inventor: Mehdi Matthew Jafari, Laguna Hills, CA (US)

(73) Assignee: Nellcor Puritan Bennett LLC, Boulder, CO (US)

( * ) Notice: Subject to any disclaimer, the term of this patent is extended or adjusted under 35 U.S.C. 154(b) by 205 days.

(21) Appl. No.: 11/421,949

(22) Filed: Jun. 2, 2006

(65) Prior Publication Data
US 2007/0278110 A1 Dec. 6, 2007

(51) Int. Cl.
G06F 17/15 (2006.01)
G06F 17/40 (2006.01)

(52) U.S. Cl. .............. 702/24; 702/22; 702/23; 702/30; 702/32

(58) Field of Classification Search .......... 702/22–24, 702/30, 32
See application file for complete search history.

(56) References Cited

U.S. PATENT DOCUMENTS

| | | | |
|---|---|---|---|
| 4,440,177 A | 4/1984 | Anderson et al. | 128/719 |
| 4,464,244 A * | 8/1984 | Uchida et al. | 204/425 |
| 4,928,684 A * | 5/1990 | Breitenfelder et al. | 128/204.21 |
| 5,003,985 A | 4/1991 | White et al. | 128/716 |
| 6,099,707 A | 8/2000 | Dunigan et al. | 204/406 |
| 6,468,211 B1 | 10/2002 | Binder | 600/301 |
| 6,497,755 B2 * | 12/2002 | Murdoch et al. | 96/110 |
| 2003/0070678 A1* | 4/2003 | Wartman et al. | 128/203.14 |
| 2003/0229290 A1 | 12/2003 | George et al. | 600/532 |

FOREIGN PATENT DOCUMENTS

EP 0672383 A2 9/1995

OTHER PUBLICATIONS

International Search Report with Written Opinion, PCT/US2007/070214, 16 pages, Dec. 11, 2007.

A.K. Demin et al., "Sensor for Measuring the Oxygen Concentration in Gas Mixtures With Unsteady Pressures," Solid State Ionics, vol. 112, pp. 355-359.

* cited by examiner

*Primary Examiner*—Hal D Wachsman
(74) *Attorney, Agent, or Firm*—Baker Botts L.L.P.

(57) ABSTRACT

A method for estimating the concentration of a particular gas in a gas mixture having a fluctuating pressure is provided. A sensor output signal indicating the concentration of a particular gas in the gas mixture is received from a gas sensor. The received sensor output signal may vary over time due to the fluctuating pressure of the gas mixture. The received sensor output signal may be processed to determine an estimate of the concentration of the particular gas in the gas mixture. The processing may include performing an autocorrelation of the signal. In some embodiments, the particular gas is oxygen and the method is used to estimate the concentration of oxygen in a gas mixture having a fluctuating pressure.

21 Claims, 11 Drawing Sheets

SYSTEM AND METHOD FOR ESTIMATING OXYGEN CONCENTRATION IN A MIXED GAS EXPERIENCING PRESSURE FLUCTUATIONS

TECHNICAL FIELD

The present disclosure is related to methods and apparatuses for measuring oxygen concentrations in a mixed gas (e.g., air), and more particularly to methods and apparatuses for measuring oxygen concentrations in a mixed gas under pressure fluctuations.

BACKGROUND

Oxygen sensors have many applications, e.g., in medical, biochemical, chemical, automotive, processing, and air quality management industries. One type of oxygen sensor is a diffusion-limited amperometric oxygen sensor for monitoring gas mixtures. These sensors are based on the operation of an electrochemical cell in a pumping mode. In particular, the oxygen concentration measurement may be governed by Faraday's law, correlating an output current with the number of oxygen ions passing through an electrolyte, and diffusion-convection partial differential equations relating an oxygen flux to gas mixture properties (e.g., $O_2$ concentration, temperature, pressure, etc.) and/or the sensor's physical geometry and dimensions.

Oxygen sensors may be used in connection with medical ventilators, device designed to provide mechanical ventilation to patients. Ventilators are used in many settings, e.g., in intensive care medicine, home care, emergency medicine (as standalone units), and for anesthesia (as a component of an anesthesia machine). A typical ventilator may include a pressurized air source, an oxygen gas source, a series of valves and tubes, and a disposable or reusable patient circuit. A valve system (e.g., a pneumatic valve) may be actuated regularly in a controlled manner to deliver a specified air/oxygen mixture to the patient several times a minute. The patient may exhale passively to release overpressure, due to the lungs' elasticity. In some ventilators, the oxygen content of inspired gas can be set from approximately 21 percent (ambient air) to 100 percent (pure oxygen). Pressure and flow characteristics can often be set mechanically and/or electronically.

Oxygen sensors may be installed in line with the patient circuit to measure the oxygen content in the gas mixture delivered to the patient. The pressure in the patient circuit may change over time based on desired settings, ventilator dynamics, patient lung characteristics, and/or the patient's breathing effort. Under steady state pressure conditions and a fixed gas mixture, oxygen molecules may pass through a sensor aperture under a diffusion mechanism, and thus the number of oxygen molecules running through the sensor (and consequently, an output current of the sensor) may approach a stationary value. However, when the gas pressure at the sensor's input aperture is fluctuating, an additional convective dynamic gas flux may arise, causing fluctuation in the number of oxygen molecules reaching the sensor cathode. As a result, the output current of the sensor may fluctuate. With a ventilator, breathing frequencies are relatively rapid (e.g., 8 to 25 breaths per minute for normal adults, and often higher frequencies for pediatric and neonatal patients), which may result in a varying (i.e., non-steady) oxygen sensor output. Various other problems with attempting to measure oxygen concentration in gas mixtures experiencing pressure fluctuations are discussed in A. K. Demin et al., "Sensor for Measuring the Oxygen Concentration in Gas Mixtures with Unsteady Pressure, *Solid State Ionics,* 112 (1998) 355-359.

Certain existing approaches for calculating estimates of oxygen concentration in a non-steady pressure environment have various limitations. For example, some approaches require time-variant nonlinear diffusive-convective partial differential equations, which may be difficult to solve. In addition, numerical approximation solutions may be computationally intensive, and thus may be impractical for implementation on a ventilator platform.

SUMMARY

A need exists for an oxygen sensor for estimating the concentration of a particular gas (e.g., oxygen) in a gas mixture experiencing a non-steady, or fluctuating, pressure.

In accordance with an embodiment of the present disclosure, a method for estimating the concentration of a particular gas in a gas mixture having a fluctuating pressure is provided. A sensor output signal indicating the concentration of a particular gas in the gas mixture is received from a gas sensor. The received sensor output signal may vary over time due to the fluctuating pressure of the gas mixture. The received sensor output signal may be processed to determine an estimate of the concentration of the particular gas in the gas mixture. The processing may include performing an autocorrelation of the signal. In some embodiments, the particular gas is oxygen and the method is used to estimate the concentration of oxygen in a gas mixture having a fluctuating pressure.

In accordance with another embodiment of the present disclosure, a system for estimating the concentration of a particular gas in a gas mixture having a fluctuating pressure is provided. The system may include a gas sensor, at least one processor, and a storage medium. The gas sensor may be adapted to interact with the gas mixture and generate a sensor output signal indicating the concentration of a particular gas in the gas mixture. The sensor output signal may varying over time due to the fluctuating pressure of the gas mixture. The at least one processor may be operatively coupled to the gas sensor. The storage media may be operatively coupled to the at least one processor, and may store instructions that, when executed by the at least one processor, cause the at least one processor to determine an estimate of the concentration of the particular gas in the gas mixture. Such determination may include performing an autocorrelation of the sensor output signal. In some embodiments, the particular gas is oxygen and the system is adapted to estimate the concentration of oxygen in a gas mixture having a fluctuating pressure.

In accordance with another embodiment of the present disclosure, computer-readable medium including computer-executable instructions for estimating the concentration of a particular gas in a gas mixture having a fluctuating pressure is provided. The instructions may include instructions for receiving from a gas sensor a sensor output signal indicating the concentration of a particular gas in the gas mixture, the received sensor output signal varying over time due to the fluctuating pressure of the gas mixture. The instructions may further include instructions for processing the received sensor output signal to determine an estimate of the concentration of the particular gas in the gas mixture, including performing an autocorrelation of the signal. In some embodiments, the particular gas is oxygen and the instructions are adapted to estimate the concentration of oxygen in a gas mixture having a fluctuating pressure.

In accordance with another embodiment of the present disclosure, a system for estimating the concentration of a particular gas in a gas mixture having a fluctuating pressure is provided. The system may include a gas sensing means, processing means, and storage means. The gas sensing means may sense a gas mixture and generate an output signal indicating the concentration of a particular gas in the gas mixture, the output signal varying over time due to the fluctuating pressure of the gas mixture. The processing means may be operatively coupled to the sensing means. The storage means may store instructions that, when executed by the processing means, cause the processing means to determine an estimate of the concentration of the particular gas in the gas mixture, including performing an autocorrelation of the sensor output signal. In some embodiments, the particular gas is oxygen and the system is adapted to estimate the concentration of oxygen in a gas mixture having a fluctuating pressure.

Further features of the disclosure, its nature and various advantages will be apparent from the accompanying drawings and the following detailed description of illustrative embodiments.

BRIEF DESCRIPTION OF THE DRAWINGS

Some embodiments of the disclosure may be understood by referring, in part, to the following description and the accompanying drawings, in which like reference numbers refer to the same or like parts and wherein.

DETAILED DESCRIPTION

Selected embodiments of the disclosure may be further understood by reference, in part, to FIGS. 1-11, wherein like numbers refer to same and like parts.

A method and apparatus for obtaining an estimate of oxygen concentration that compensates for pressure fluctuations may be based on the observation that, for a particular time interval, pressure fluctuations associated with mechanical ventilation may be considered an approximately cyclostationary process that results in corresponding cyclostationary fluctuations in the uncompensated oxygen sensor output. Accordingly, the cyclostationary pressure variations during consecutive breathing cycles (inhalation and exhalation) may result in corresponding cyclostationary fluctuations in the number of oxygen molecules reaching the sensor cathode. Therefore, in an environment with a substantially fixed $O_2$ content and cyclostationary pressure fluctuations, the apparent oxygen concentration measured by the sensor (e.g., based on a sensor output current) may demonstrate a cyclostationary behavior.

A zero difference autocorrelation of the apparent oxygen concentration computed from the sensor output current may approach a constant value as a function of the true $O_2$ concentration. A "zero difference autocorrelation," as may be generally known in the art, may refer to an average of the product of the signal with itself, i.e., zero delay. The square root (or root mean square) of the zero difference autocorrelation of the sensor's apparent concentration measurement may be a reasonable estimate of the true oxygen concentration of the gas mixture. (For example, for test conditions used under stable conditions, results were found to be within 0-3 percentage points of the actual percent oxygen concentration.)

Figure 1:
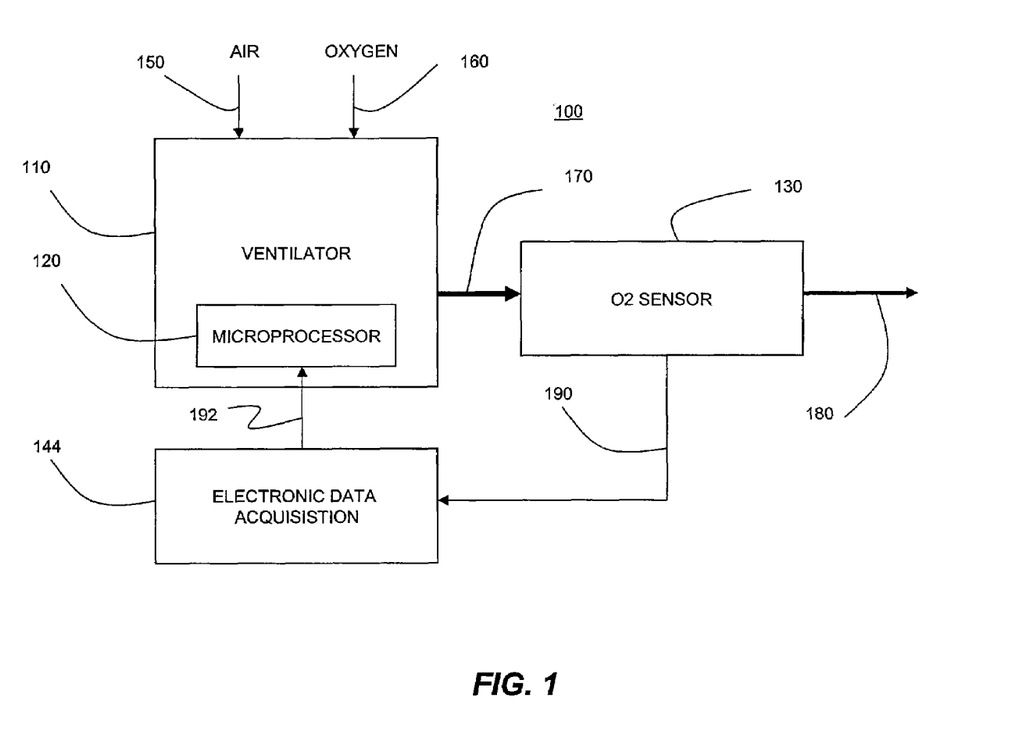
FIG. 1 is a schematic view of the system in accordance with an example embodiment of the present disclosure.

FIG. 1 illustrates an example system 100 for estimating oxygen concentration in a non-steady pressure environment, in accordance with one embodiment. System 100 may include a ventilator 110, a microprocessor 120, an $O_2$ sensor 130, and an electronic data acquisition system 144. Although the present embodiment is described in connection with a ventilator 110, it may be understood that ventilator 110 may be optional. In addition, although this document focuses on sensors for use with a ventilator, ventilator 110 may comprise any other suitable medical device or system. In addition, as used throughout this document, the term "ventilator" may refer to any device, apparatus, or system for delivering breathing gas to a patient, e.g., a ventilator, a respirator, a CPAP device, or a BiPAP device. In an example embodiment, ventilator 110 may be a Model 840 NPB critical care ventilator from Tyco Healthcare, Nellcor Puritan Bennett, Pleasanton, Calif.

Ventilator 110 may regulate the ratio of mixed gas (e.g., a mixture of air 150 and $O_2$ 160) delivered to the patient, e.g., using an internal microprocessor 120. Pressurized air 150 and oxygen gas 160 may be supplied to, or generated by, the ventilator in any suitable manner. For example only, pressurized air 150 may be generated by ventilator 110 and oxygen gas 160 may be supplied by an oxygen tank. In example embodiments, ventilator 110 may be a microprocessor-based device (e.g., a Motorola 68040 microprocessor) that includes two independent central processing units: one for managing breath delivery according to specified variables and another for managing user interface functions, e.g., ventilator settings and/or patient data monitoring.

The term "patient" may refer to any person who is receiving breathing support, regardless of the medical status, official patient status, physical location, or any other characteristic of the person. Thus, for example, patients may include persons under official medical care (e.g., hospital patients), persons not under official medical care, persons receiving care at a medical care facility, persons receiving home care, etc.

$O_2$ sensor 130 may provide a measurement of the oxygen concentration of the mixed gas delivered to the patient (indicated by line 180). $O_2$ sensor 130 may be positioned at the output of ventilator 110 (indicated by line 170) to obtain oxygen measurements. $O_2$ sensor 130 may be powered by the electrical circuitry of ventilator 110, or otherwise.

Figure 2:
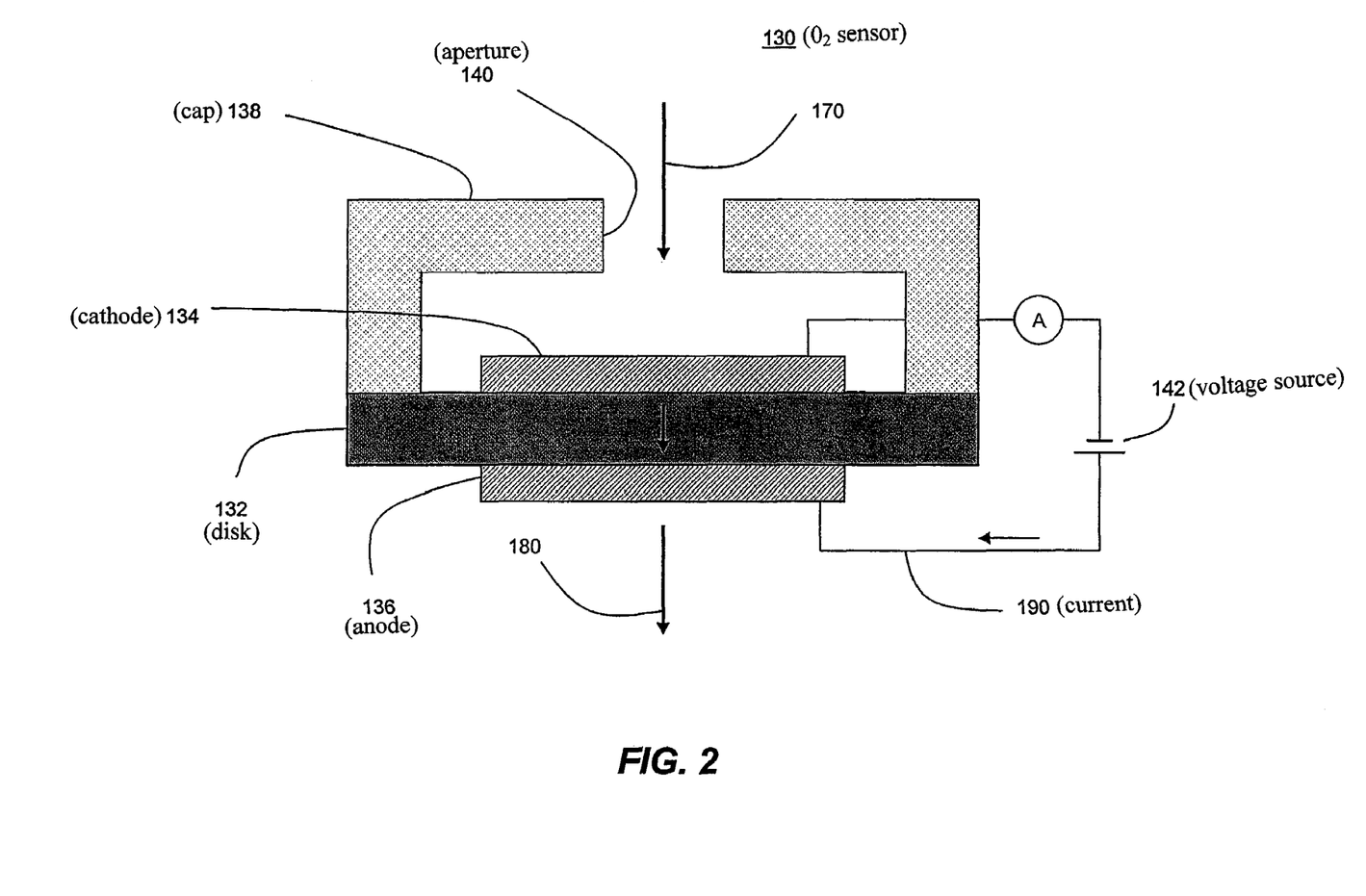
FIG. 2 is a view of an oxygen sensor of the system of FIG. 1.

FIG. 2 illustrates an example $O_2$ sensor 130, in accordance with one embodiment. $O_2$ sensor 130 may include an electrolyte disk 132 positioned between a cathode 134 and an anode 136, a heater, and a cap 138 having an aperture 140. In some embodiments, electrolyte disk 132 may be formed from a material that allows movement of oxygen ions after being heated to a high temperature. For example, the electrolyte may comprise partially stabilized zirconia heated to a temperature of about 550° C. When a voltage is applied to sensor 130 via a voltage source 142, oxygen may move through electrolyte disk 132 from the cathode side (134) to the anode side (136) because the carriers of the current flowing through disk 132 are oxygen ions. The size of aperture 140 may serve to limit gas diffusion to the cathode side (134) and may thus limit the transfer of oxygen ions through the electrolyte. As a result, the sensor output current may be likewise limited. Under fixed temperature and steady state pressure conditions, the sensor output current may be proportional to a function of the gas mixture oxygen concentration. An example oxygen sensor may be a diffusion-limited amperometric oxygen sensor, e.g., a diffusion-limited amperometric oxygen sensor manufactured by Electrovac AG of Austria.

The approach described herein may apply at least to sensors having an output that varies in synchrony, even if scaled and time-delayed, with the gas mixture pressure waveform. Further, the approach may apply to situations in which the pressure fluctuations are cyclostationary (i.e., repeating in a regular fashion), such as may be common with mechanical ventilation.

The steady state output current of $O_2$ sensor 130 may be approximated as follows:

$$I_{ss} = -k * \ln\left(1 - \frac{[O_2]}{100}\right) \quad [1]$$

where $I_{ss}$ is the steady state current in amperes, $[O_2]$ is the percent volumetric oxygen concentration, and k is a calibration constant.

The electrical output of $O_2$ sensor 130 may be indicated at line 190. The sensor may generate current (Amperes) corresponding to the movement of oxygen ions. The output may be communicated to an electronic data acquisition system 144, which may include analog-to-digital data conversion and/or signal noise filtering. The sensor output current 190 may be measured in any suitable manner, e.g., using a commercial ammeter or by conversion to a measurable voltage using an operational amplifier circuit. Appropriate sensor driver circuitry (e.g., circuitry provided by Electrovac AG) may be used. Output voltage may be filtered (e.g., for antialiasing and/or noise reduction purposes) and digitized by suitable A/D circuitry. The digitized signal data may then be communicated to internal microprocessor 120 (or other computer or processor) for signal processing, as indicated by line 192. In some embodiments, the data may be processed by a breath delivery processor of the ventilator.

Microprocessor 120 (or other computer or processor) may process the received digitized signal data to compute oxygen concentration in a non-steady pressure environment using one or more oxygen concentration algorithms. Examples of such oxygen concentration algorithms are shown below as equations [2]-[5]. Such algorithms may be stored or coded in the computing device (microprocessor 120 or other computer or processor) or any suitable memory or storage device.

Microprocessor 120 or other computer or processor may perform the oxygen concentration computations (e.g., execute the oxygen concentration algorithms) using appropriate software or other instructions stored in an associated memory. In various embodiments, such data may be processed by any suitable means, e.g., using a spreadsheet application (e.g., Excel), and/or using a computer to run executable software routines in any language (e.g., C or C++). In some embodiments, a stand-alone device may be used to perform the oxygen concentration computations. In such applications, the stand-alone device may include a processor operable to acquire the relevant input data (e.g., from the ventilator) and execute the coded algorithms. In another embodiment, one or more oxygen concentration algorithms may be executed at least partially manually.

According to an example embodiment, a predetermined duration (e.g., a "moving window") may be used to estimate the true $O_2$ concentration ($C_{estimate}$). At each sampling cycle of discrete time i, the sequential calculations disclosed in equations [2]-[5] may be performed. Equation [2] defines a function X(i) as follows:

$$X(i) = -\frac{I(i)}{k} \quad [2]$$

where k is a sensor calibration constant, and I(i) represents the sensor output current (Amps) at time i. In an example embodiment, a moving window of 30 seconds or 5 breath cycles may be used, and the sampling cycle may be 5 ms. (30 seconds or 5 breaths may represent a reasonable window for a human breathing pattern). Different moving window parameters may be used, as appropriate.

The sensor calibration constant k may be computed in any suitable manner. For example, the sensor calibration constant k may be computed as follows. A gas mixture with a known oxygen concentration (e.g., 21%) may be passed by $O_2$ sensor 130 while maintaining a constant pressure in the pneumatic circuit. (In FIG. 1, lines 170 and 180 represent the pneumatic circuit that delivers the gas mixture to the patient. In an example embodiment, oxygen sensor 130 may be connected to the circuit via a manifold installed adjacent to the ventilator output and exposed to the gas mixture flowing through the circuit via an opening.) The sensor output current I(i), indicated as 190, may be measured at regular periods (e.g., every 0.005 second). Readings for a certain time interval (e.g., 1 second) may be stored. These stored readings and the known oxygen concentration may be input into the sensor equation (see equation [1], above) to calculate the sensor constant for each reading. The average of all the computed values may be used as the sensor constant k. In experimental testing, the calibration constant k for an example sensor was determined to be 1.08. The calibration constant k for any particular sensor may have any suitable value.

A pair of functions, $Y_1(i)$ and $Y_2(i)$, may be calculated from X(i), as indicated in equations [3] and [4]:

$$Y_1(i) = \exp(X(i)) \quad [3]$$

$$Y_2(i) = Y_1(i) * Y_1(i) \quad [4]$$

Further, an average $Y_1$ value ($Y_1$bar) may be calculated as $Y_1$ averaged over the moving window of N values, and an average $Y_2$ value ($Y_2$bar) may be calculated as $Y_2$ averaged over the moving window of N values. The estimate of the true $O_2$ concentration ($C_{estimate}$) may then be determined from equation [5]:

$$C_{estimate} = 100 * \sqrt{a_1 + a_2 * Y_1\text{bar} + a_3 * Y_2\text{bar}} \quad [5]$$

where $a_1 = 1.0$; $a_2 = -2.0$; and $a_3 = 1.0$. The constants $a_1$, $a_2$, and $a_3$ were determined using the algorithms shown above, beginning with equation [1] and calculating the RMS function (root mean square of the zero difference autocorrelation) for the $O_2$ concentration.

The "moving window" buffer may be reset after particular events, such as a ventilator settings change event, for example. (In the example discussed above, the moving window buffer is the 30-second buffer of data points saved in memory). A ventilator settings change event may refer to one or more changes in relevant ventilator settings.

It may be understood that the various values used in equations [1]-[5], e.g., constants $a_1$, $a_2$, $a_3$; the moving window; and/or a resetting strategy (i.e., conditions and/or criteria for complete or partial resetting of particular values to specific numbers, described herein are merely example, and such values may be selected and/or adjusted as appropriate to one skilled in the art.

Figure 3:
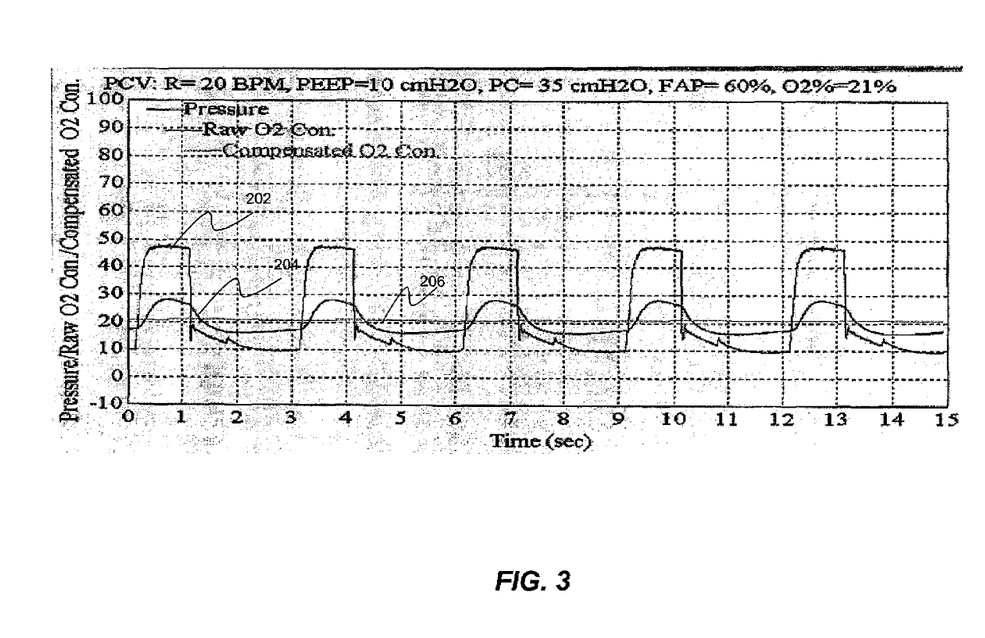
FIGS. 3-10 illustrate sample fluctuating signals for use by the system to estimate oxygen concentration, in accordance with an example embodiment of the present disclosure.

FIGS. 3-10 illustrate sample plots indicating raw sensor output and compensated $O_2$ concentration values (i.e., estimated true $O_2$ concentration values) for various ventilation conditions. For example, FIG. 3 represents a case in which PCV:R=20 breaths per minute (BPM); PEEP=10 cm $H_2O$; PC=35 cm $H_2O$; FAP=60%; and $O_2$%=21%. "PCV" refers to Pressure Control Ventilation modality; "R" refers to respiratory rate; "PEEP" refers to positive end expiratory pressure (ventilator setting); "PC" refers to pressure control target (ventilator setting); "FAP" refers to flow acceleration percent (ventilator setting for rate of pressurization); and "O2%" refers to desired $O_2$ concentration (ventilator setting.)

As shown in FIG. 3, a circuit pressure proximal to the patient over time is indicated as 202. As used herein, circuit pressure generally refers to the estimated or measured gas pressure in the gas delivery tubing at a location proximate the circuit connection to the patient interface (e.g., tracheal tube or mask) The raw $O_2$ concentration is indicated as 204, which may represent the result of processing sensor output 192 of electronic data acquisition 140 using equation [2]. The compensated $O_2$ concentration is indicated as 206, which may represent the result of equation [5], e.g., as output by microprocessor 120 or other computer or processor. As indicated by compensated $O_2$ concentration 206, fluctuations in the raw concentration signal 204 are substantially rectified and the fixed concentration may be estimated by compensating for pressure fluctuations.

Figure 4:
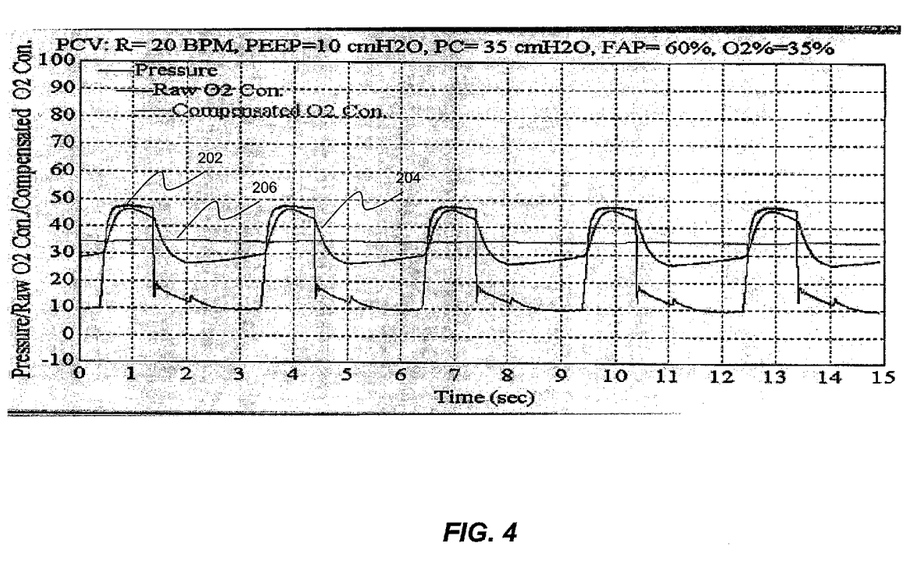
Figure 5:
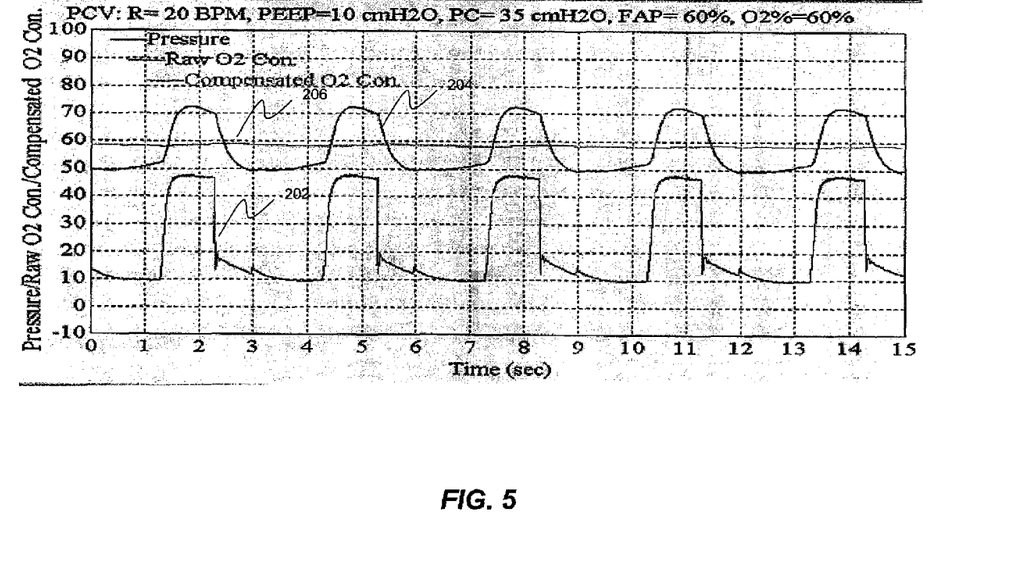
Figure 6:
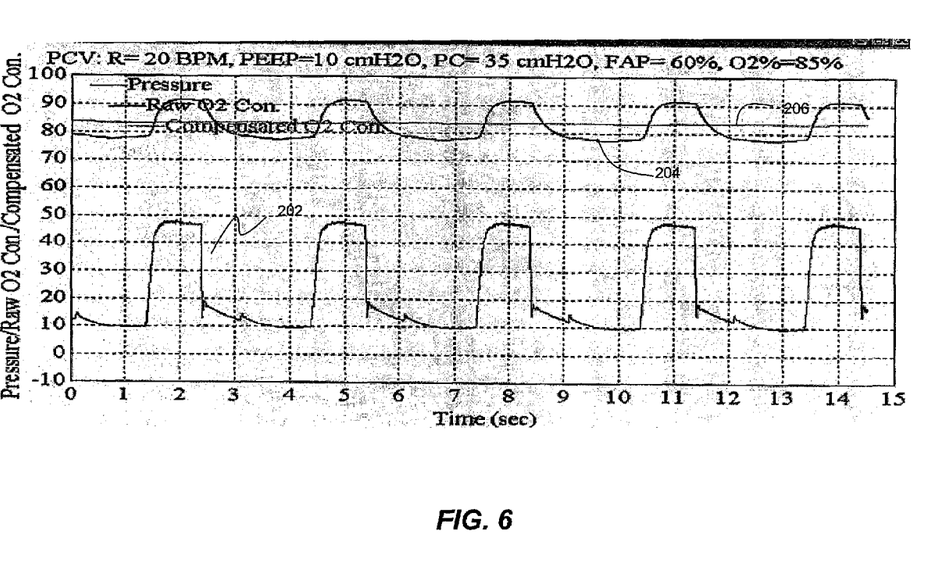
Figure 7:
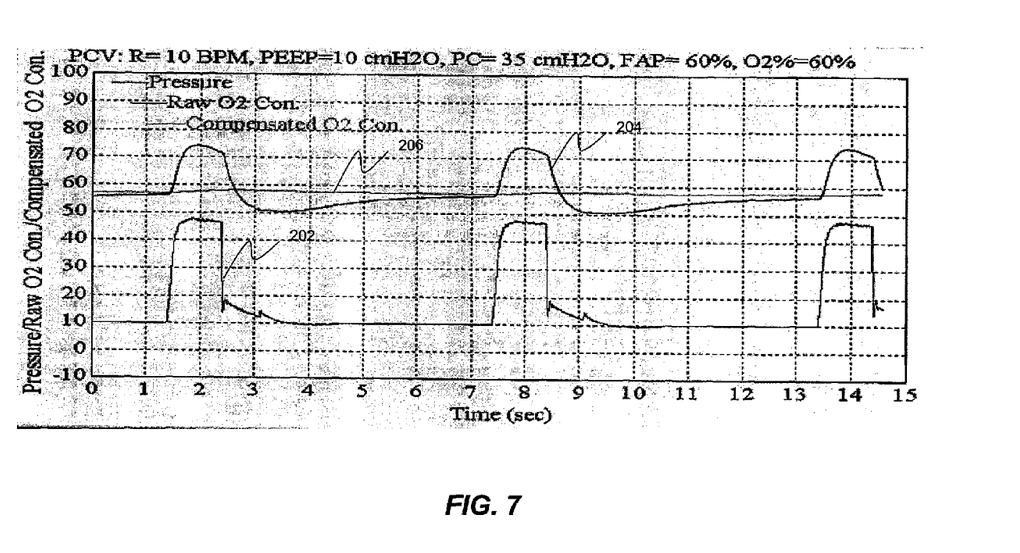
Figure 8:
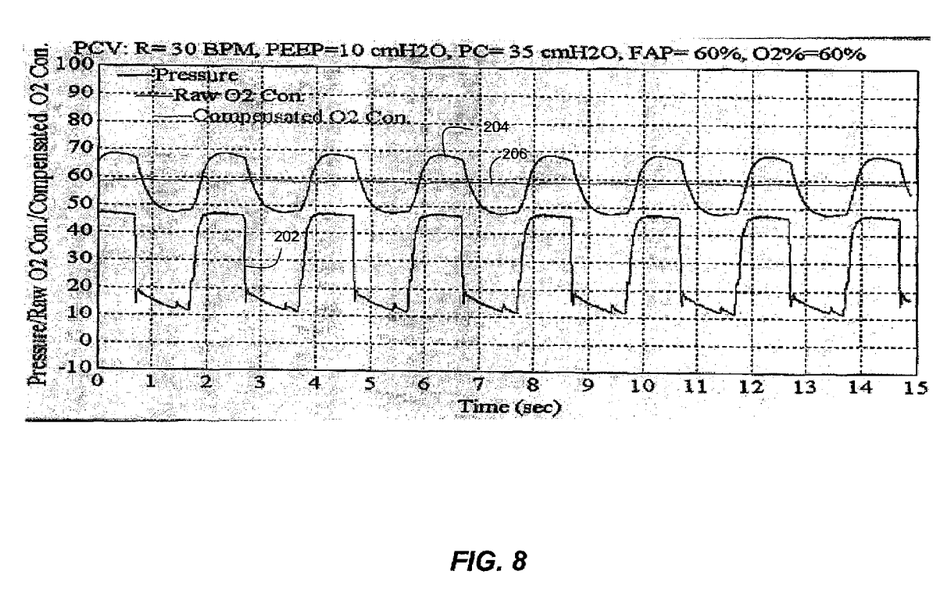
Figure 9:
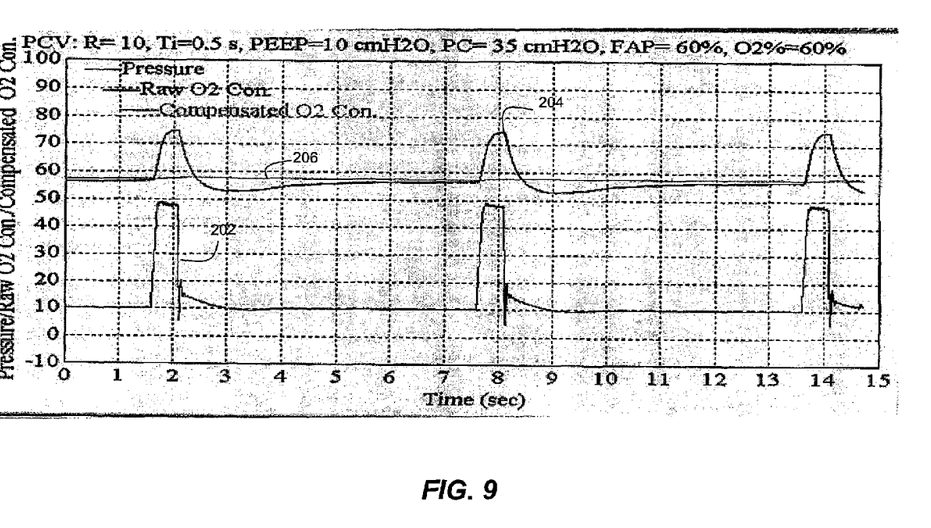
Figure 10:
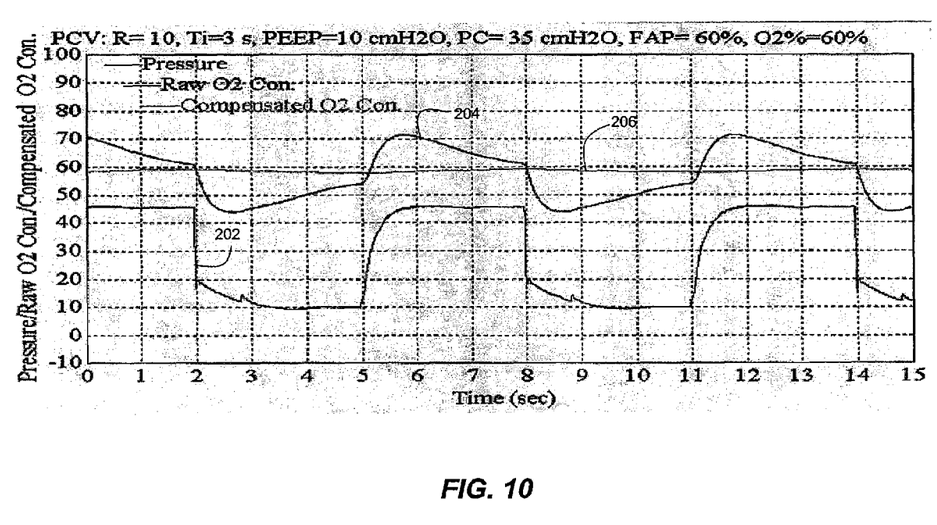

FIGS. 4, 5, and 6 illustrate situations similar to that of FIG. 3, except the oxygen concentration is set at 35%, 60% and 85%, respectively. FIGS. 7 and 8 illustrate situations similar to that of FIG. 5, except the rate R is set at 10 and 30 breaths per minute, respectively. FIGS. 9 and 10 illustrate situations similar to that of FIG. 6, except Ti=0.5 sec in FIG. 8, Ti=3 sec in FIG. 9, and Ti=1 sec in FIG. 6. (As may be known in the art, Ti is the inspiratory duration, which may be a ventilator setting.)

The situations illustrated in FIGS. 3-10 are examples only, and the methods discussed herein for estimating true $O_2$ concentration values in a fluctuating pressure environment may be similarly applied in any other suitable situation and/or using any other parameter settings and/or values.

Figure 11:
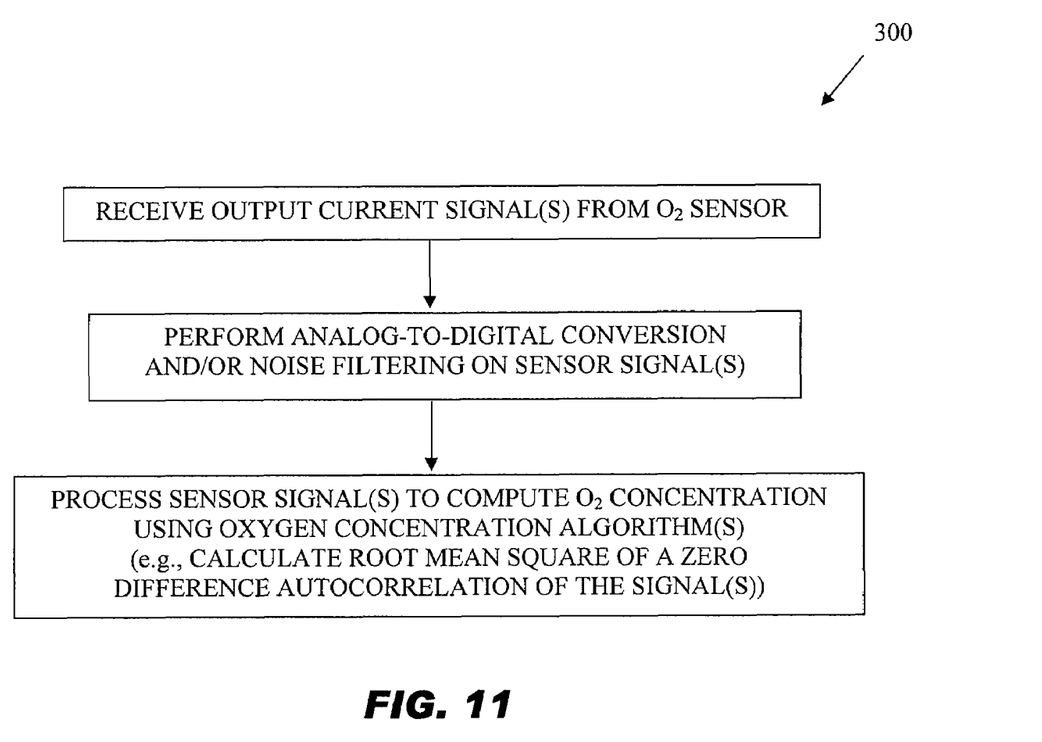
FIG. 11 is a flow chart illustrating an example method of estimating oxygen concentration in a gas mixture, in accordance with an example embodiment of the present disclosure.

FIG. 11 is a flow chart illustrating an example method of estimating oxygen concentration in a gas mixture, in accordance with an example embodiment of the present disclosure.

Although the discussion above focuses on determining the concentration of oxygen in a mixed gas, it should be understood that some or all of the systems, methods, techniques, and/or algorithms discussed herein may be used for determining the concentration of one or more other particular gasses in a mixed gas. In addition, although the discussion above focuses on determining the concentration of oxygen in a mixed gas experiencing cyclostationary fluctuations, it should be understood that some or all of the systems, methods, techniques, and/or algorithms discussed herein may be used for determining the concentration of oxygen (or other particular gas) in a mixed gas experiencing other types of regular and/or irregular fluctuations (i.e., non-cyclostationary fluctuations).

Although the disclosed embodiments have been described in detail, it should be understood that various changes, substitutions and alterations can be made herein without departing from the spirit and scope of the disclosure as illustrated by the following claims.

What is claimed is:

1. A method for estimating gas concentration in a gas mixture having a fluctuating pressure, comprising:
    receiving from a gas sensor a sensor output signal indicating the concentration of a particular gas in the gas mixture, the received sensor output signal varying over time due to the fluctuating pressure of the gas mixture; and
    processing the received sensor output signal to determine an estimate of the concentration of the particular gas in the gas mixture, wherein determining an estimate of the concentration includes determining the square root of a zero difference autocorrelation of the sensor output signal.

2. A method according to claim 1, wherein the particular gas is oxygen and the sensor output signal is received from an oxygen sensor.

3. A method according to claim 2, wherein the sensor output signal is received from a diffusion-limited amperometric oxygen sensor.

4. A method according to claim 2, wherein:
    the sensor output signal is received from an oxygen sensor comprising an electrolyte; and
    the received sensor output signal corresponds to a quantity of oxygen passing through the electrolyte.

5. A method according to claim 1, wherein the received sensor output signal comprises a current signal representative of the concentration of the particular gas in the gas mixture, the current signal varying over time due to the fluctuating pressure of the gas mixture.

6. A method according to claim 5, wherein the received current signal varies in a cyclostationary manner corresponding to cyclostationary fluctuations of the pressure of the gas mixture.

7. A method according to claim 1, wherein processing the received sensor output signal comprises performing at least one of an analog-to-digital data conversion process and a signal noise filtering process prior to performing the autocorrelation of the sensor output signal.

8. A method according to claim 1, wherein determining an estimate of the concentration of the particular gas in the gas mixture comprises sampling the sensor output signal over a predetermined interval.

9. A method according to claim 1, wherein:
    the fluctuating pressure of the gas mixture corresponds to breathing cycles of a patient; and
    determining an estimate of the concentration of the particular gas in the gas mixture comprises sampling the sensor output signal over a predetermined number of breathing cycles of the patient.

10. A system for estimating gas concentration in a gas mixture having a fluctuating pressure, comprising:
    a gas sensor adapted to interact with the gas mixture and generate a sensor output signal indicating the concentration of a particular gas in the gas mixture, the sensor output signal varying over time due to the fluctuating pressure of the gas mixture;
    at least one processor operatively coupled to the gas sensor; and
    tangible storage media operatively coupled to the at least one processor, the tangible storage media storing computer-executable instructions for determining an estimate of the concentration of the particular gas in the gas mixture, wherein determining an estimate of the concentration includes determining the square root of a zero difference autocorrelation of the sensor output signal.

11. A system according to claim 10, wherein the particular gas is oxygen and the gas sensor is an oxygen sensor.

12. A system according to claim 11, wherein the oxygen sensor is a diffusion-limited amperometric sensor.

13. A system according to claim 11, wherein:
the oxygen sensor comprises an electrolyte; and
the sensor output signal corresponds to a quantity of oxygen passing through the electrolyte.

14. A system according to claim 10, wherein the sensor output signal comprises a current signal representative of the concentration of the particular gas in the gas mixture, the current signal varying over time due to the fluctuating pressure of the gas mixture.

15. A system according to claim 14, wherein the current signal varies in a cyclostationary manner corresponding to cyclostationary fluctuations of the pressure of the gas mixture.

16. A system according to claim 10, wherein the at least one processor is operable to perform at least one of an analog-to-digital data conversion process and a signal noise filtering process prior to performing the autocorrelation of the sensor output signal.

17. A system according to claim 10, wherein determining an estimate of the concentration of the particular gas in the gas mixture comprises determining a zero difference autocorrelation of the sensor output signal.

18. A system according to claim 10, wherein determining an estimate of the concentration of the particular gas in the gas mixture comprises sampling the sensor output signal over a predetermined interval.

19. A system according to claim 10, wherein:
the fluctuating pressure of the gas mixture corresponds to breathing cycles of a patient; and
determining an estimate of the concentration of the particular gas in the gas mixture comprises sampling the sensor output signal over a predetermined number of breathing cycles of the patient.

20. A tangible computer-readable storage medium including computer-executable instructions for estimating gas concentration in a gas mixture having a fluctuating pressure, comprising:
instructions for receiving from a gas sensor a sensor output signal indicating the concentration of a particular gas in the gas mixture, the received sensor output signal varying over time due to the fluctuating pressure of the gas mixture; and
instructions for processing the received sensor output signal to determine an estimate of the concentration of the particular gas in the gas mixture, wherein determining an estimate of the concentration includes determining the square root of a zero difference autocorrelation of the sensor output signal.

21. A system for estimating gas concentration in a gas mixture having a fluctuating pressure, comprising:
gas sensing means for sensing a gas mixture and generating an output signal indicating the concentration of a particular gas in the gas mixture, the output signal varying over time due to the fluctuating pressure of the gas mixture;
processing means operatively coupled to the gas sensing means; and
tangible storage means for storing instructions that, when executed by the processing means, cause the processing means to determine an estimate of the concentration of the particular gas in the gas mixture, wherein determining an estimate of the concentration includes determining the square root of a zero difference autocorrelation of the output signal generated by the gas sensing means.

* * * * *